US00PP36564P2

(12) United States Plant Patent
Danziger

(10) Patent No.: US PP36,564 P2
(45) Date of Patent: Mar. 18, 2025

(54) ***SALVIA* PLANT NAMED 'DPWSAFUWHT'**

(50) Latin Name: *Salvia farinacea*
Varietal Denomination: DPWSAFUWHT

(71) Applicant: Gavriel Danziger, Moshav Mishmar Hashiva (IL)

(72) Inventor: Gavriel Danziger, Moshav Mishmar Hashiva (IL)

(73) Assignee: DANZIGER "DAN" FLOWER FARM, Beit Dagan (IL)

( * ) Notice: Subject to any disclaimer, the term of this patent is extended or adjusted under 35 U.S.C. 154(b) by 0 days.

(21) Appl. No.: 18/755,613

(22) Filed: Jun. 26, 2024

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Salvia* plant named 'DPWSAFUWHT', characterized by its tall and upright plant habit; vigorous growth habit and rapid growth rate; freely branching habit; dark green-colored leaves; freely flowering habit; long and erect inflorescences with numerous white-colored flowers; and excellent container and garden performance.

2 Drawing Sheets

Figure 1:
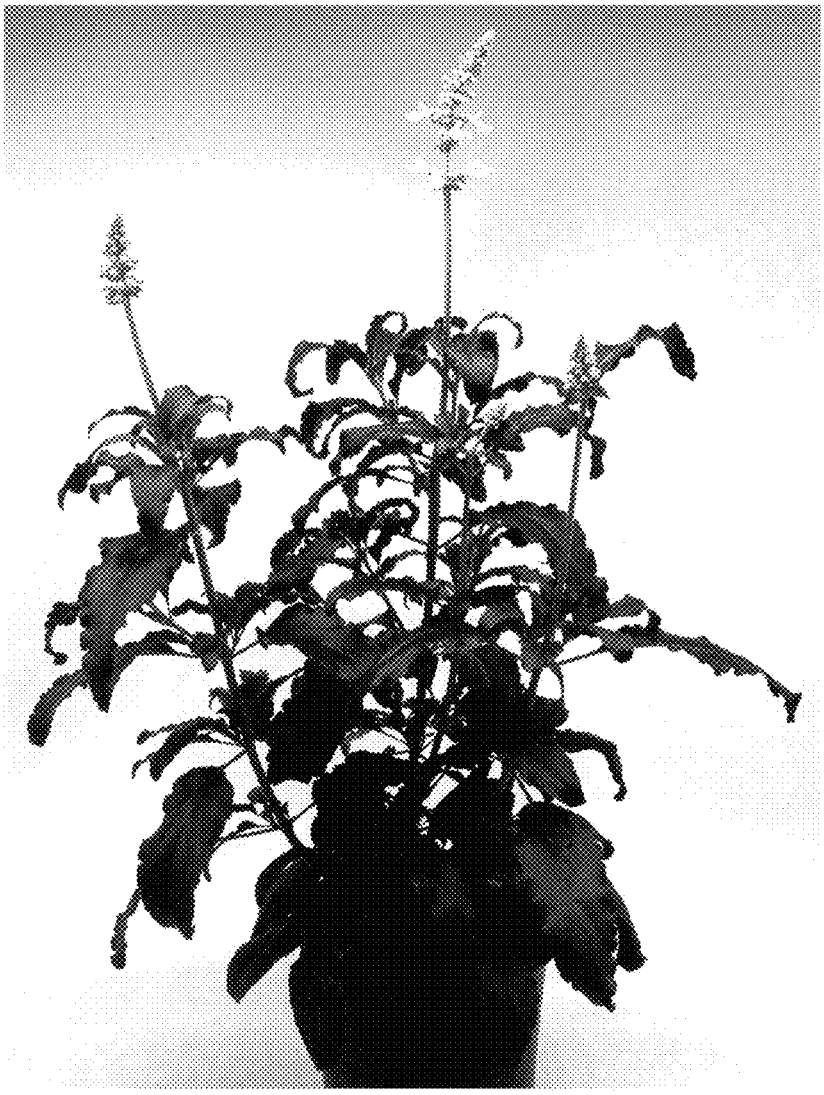

Botanical designation: *Salvia farinacea.*
Cultivar denomination: 'DPWSAFUWHT'.

BACKGROUND OF THE INVENTION

The present invention relates to a new and distinct cultivar of *Salvia* plant, botanically known as *Salvia farinacea* and hereinafter referred to by the name 'DPWSAFUWHT'.

The new *Salvia* plant is a product of a planned breeding program conducted by the Inventor in Moshav Mishmar Hashiva, Israel. The objective of the breeding program is to create new freely branching *Salvia* plants with attractive leaves and flowers and good garden performance.

The new *Salvia* plant originated from an open-pollination in 2018 of a proprietary selection of *Salvia farinacea* identified as code number SAF-9-971, not patented, as the female, or seed, parent with an unknown proprietary selection of *Salvia farinacea* as the male, or pollen, parent. The new *Salvia* plant was discovered and selected by the Inventor as a single flowering plant from within the progeny of the stated open-pollination in a controlled greenhouse environment in Moshav Mishmar Hashiva, Israel in June 2019.

Asexual reproduction of the new *Salvia* plant by vegetative terminal cuttings in Moshav Mishmar Hashiva, Israel since 2019 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DPWSAFUWHT'. These characteristics in combination distinguish 'DPWSAFUWHT' as a new and distinct *Salvia* plant:

1. Tall and upright plant habit.
2. Vigorous growth habit and rapid growth rate.
3. Freely branching habit.
4. Dark green-colored leaves.
5. Freely flowering habit.
6. Long and erect inflorescences with numerous white-colored flowers.
7. Excellent container and garden performance.

Plants of the new *Salvia* can be compared to plants of the female parent selection. Plants of the new *Salvia* differ primarily from plants of the female parent selection in leaf shape as leaves of plants of the new *Salvia* are more narrow than leaves of plants of the female parent selection. In addition, leaves of plants of the new *Salvia* are more curled than leaves of plants of the female parent selection.

Plants of the new *Salvia* can be compared to plants of *Salvia farinacea* 'DSALDPOCN', disclosed in U.S. Plant Pat. No. 28,121. In side-by-side comparisons, plants of the new *Salvia* differ from plants of 'DSALDPOCN' in the following characteristics:

1. Plants of the new *Salvia* have longer inflorescences than plants of 'DSALDPOCN'.
2. Flowers of plants of the new *Salvia* are white in color whereas flowers of plants of 'DSALDPOCN' are deep violet blue in color.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the colors of the new *Salvia* plant.

The photograph on the first sheet (FIG. 1) is a side perspective view of a typical flowering plant of 'DPWSA-FUWHT' grown in a container.

Figure 2:
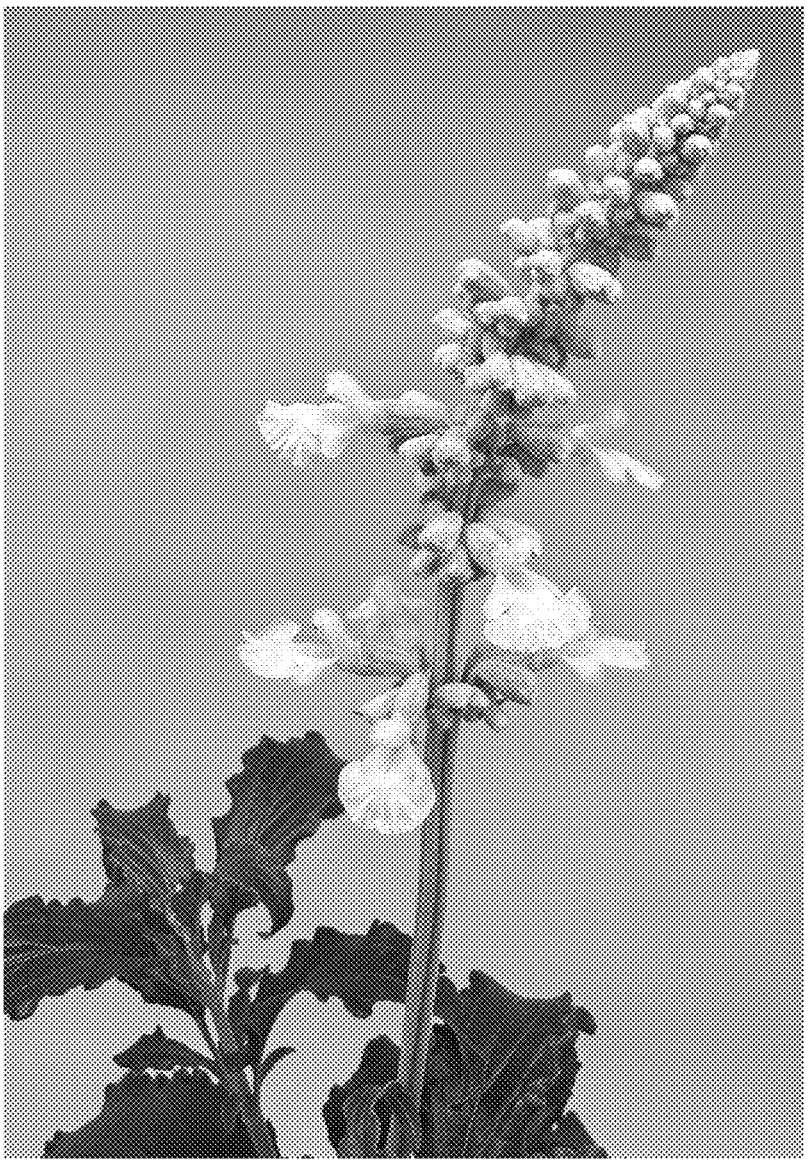

The photograph on the second sheet (FIG. 2) is a close-up view of a typical inflorescence of 'DPWSAFUWHT'.

DETAILED BOTANICAL DESCRIPTION

The aforementioned photographs and following observations and measurements describe plants grown during the late winter and early spring in 10.75-cm containers in a glass-covered greenhouse in Loudon, New Hampshire and under cultural practices typical of commercial *Salvia* production. During the production of the plants, day and night temperatures averaged 20° C. Plants were eight weeks from planting rooted cuttings when the photographs and description were taken. In the following description, color references are made to The Royal Horticultural Society Colour Chart, 2015 Edition, except where general terms of ordinary dictionary significance are used.

Botanical classification: *Salvia farinacea* 'DPWSA-FUWHT'.

Parentage:

*Female, or seed, parent*.—Proprietary selection of *Salvia farinacea* identified as code number SAF-9-971, not patented.

*Male, or pollen, parent*.—Unknown proprietary selection of *Salvia farinacea*, not patented.

Propagation:

*Type*.—By vegetative terminal cuttings.

*Time to initiate roots, summer*.—About four to seven days at temperatures ranging from about 25° C. to 30° C.

*Time to initiate roots, winter*.—About six to ten days at temperatures ranging from about 10° C. to 25° C.

*Time to produce a rooted young plant from unrooted cuttings, summer*.—About 14 to 21 days at temperatures ranging from about 25° C. to 30° C.

*Time to produce a rooted young plant from unrooted cuttings, winter*.—About 21 to 30 days at temperatures ranging from about 10° C. to 25° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; tall and upright plant habit; vigorous growth habit and rapid growth rate.

*Branching habit*.—Freely basal branching with about two to three primary lateral branches with secondary lateral branches potentially developing at every node; relatively bushy and dense appearance.

*Plant height*.—About 51 cm to 58 cm.

*Plant width*.—About 30 cm to 35 cm.

*Lateral branch description*.—Length: About 38 cm to 42 cm. Diameter, at the base: About 5 mm to 5.5 mm. Internode length: Variable, about 5 cm to 7.5 cm. Strength: Strong, sturdy, flexible; not brittle. Aspect: Mostly upright, erect to about 25° from vertical. Texture and luster: Densely pubescent; pubescence, fine; longitudinally ridged; semi-glossy. Color, developing and developed: Close to 146A.

Leaf description:

*Arrangement*.—Opposite, simple.

*Length*.—About 11 cm to 12 cm.

*Width*.—About 4.5 cm to 5 cm.

*Shape*.—Elongated ovate; curled.

*Apex*.—Sharply acute.

*Base*.—Broadly attenuate to cuneate.

*Margin*.—Crenate; undulate.

*Texture and luster, upper surface*.—Smooth, glabrous; glossy.

*Texture and luster, lower surface*.—Smooth, glabrous; moderately glossy.

*Venation pattern*.—Pinnate, reticulate.

*Color*.—Developing leaves, upper surface: Close to 147A. Developing leaves, lower surface: Close to between 147B and 146A. Fully expanded leaves, upper surface: Close to between 147A and 139A; venation, close to between 147A and 139A. Fully expanded leaves, lower surface: Close to 147A; venation, close to 147B.

*Petioles*.—Length: About 3 mm to 3.3 mm. Diameter: About 2 mm. Strength: Strong; flexible. Texture and luster, upper and lower surfaces: Densely pubescent; pubescence, fine; slightly glossy. Color, upper surface: Close to 144A. Color, lower surface: Close to 144A and 144B.

Flower description:

*Flower arrangement and shape*.—Single bilabiate flowers arranged on erect terminal and axillary racemes; freely flowering habit with about 10 to 15 flowers per alternate clusters, at least 20 clusters per inflorescence and about 200 to 300 flowers developing per inflorescence; flowers face mostly outwardly.

*Fragrance*.—Faint; pleasant and sweet.

*Natural flowering season*.—Early flowering habit; depending on temperature, plants begin flowering about six to seven weeks after planting rooted young plants; plants flower from late spring until frost in the garden in New Hampshire.

*Flower longevity*.—Depending on temperature, flowers last about five to seven days on the plant; flowers persistent.

*Inflorescence buds*.—Length: About 3 cm. Diameter: About 1.6 cm. Shape: Conical. Texture and luster: Pubescent; velvety; slightly glossy. Color: Close to 193A.

*Inflorescence height*.—About 15.5 cm.

*Inflorescence diameter*.—About 3.75 cm to 4.5 cm.

*Flower buds*.—Length: About 6 mm. Diameter: About 3 mm. Shape: Obovate. Texture and luster: Pubescent; velvety; slightly glossy. Color: Close to 193A.

*Flower diameter*.—About 1 cm.

*Flower height*.—About 1.5 cm to 2 cm.

*Flower throat diameter*.—About 2 mm to 3 mm.

*Flower tube length*.—About 1 cm.

*Flower tube diameter, proximally*.—About 3 mm.

*Petals*.—Arrangement: Bi-labiate petals fused forming an upper galea and three lower petals fused forming a broader lower protruding lip. Upper galea: Length:

About 5 mm. Width: About 3 mm. Shape: Oblong; overall shape, hood-like. Apex: Round, obtuse. Base: Fused. Margin: Entire; not undulate. Texture and luster, upper and lower surfaces: Densely pubescent; matte. Color: When developing and fully developed, upper surface: Close to NN155C to NN155D. When developing and fully developed, lower surface: Close to NN155C to NN155D. Lower lip: Length: About 9 mm to 10 mm. Width: About 9 mm to 10 mm. Shape: Spatulate. Apex: Broadly obtuse with random emarginations. Base: Fused. Margin: Entire; undulate; occasionally with a single indentation. Texture and luster, upper and lower surfaces: Smooth, glabrous; slightly glossy to matte; slightly iridescent. Color: When developing and fully developed, upper surface: Close to NN155D; towards the center, close to 144D. When developing and fully developed, lower surface: Close to NN155D; towards the base, slightly and variably tinged with close to 144D. Throat, texture and luster: Smooth, glabrous; slightly glossy to matte. Throat color: Close to NN155D. Tube, texture and luster: Sparsely pubescent; slightly glossy. Tube color: Close to NN155D.

*Calyx*.—Arrangement: Single whorl of two sepals fused towards the base into a tubular calyx. Calyx length: About 7.5 mm to 8 mm. Calyx diameter: About 3 mm. Sepal length: About 7.5 mm to 8 mm. Sepal width: About 1 mm. Sepal shape: Linear. Sepal apex: Truncate. Sepal margin: Free part, entire. Sepal texture and luster, inner surface: Smooth, glabrous; matte. Sepal texture and luster, outer surface: Densely pubescent; slightly glossy to matte. Color: When developing and fully developed, inner surface: Close to 144A. When developing and fully developed, outer surface: Close to 193A.

*Peduncles*.—Length: About 24 cm to 31 cm. Diameter: About 3.5 mm to 5 mm. Strength: Strong, flexible. Aspect: Mostly erect. Texture and luster: Densely pubescent; pubescence, fine; semi-glossy. Color: Close to 146A.

*Pedicels*.—Length: About 3 mm. Diameter: About 1 mm. Strength: Strong, flexible. Aspect: About 45° from peduncle axis. Texture and luster: Moderately to densely pubescent; semi-glossy. Color: Close to 146A.

*Reproductive organs*.—Stamens: Quantity per flower: Two. Filament length: About 9 mm. Filament color: Close to NN155D. Anther size: About 0.5 mm by 1 mm. Anther shape: Oblong. Anther color: Close to 145C. Pollen amount: If present, scarce. Pollen color: Close to 7A. Pistils: Quantity per flower: One. Pistil length: About 8 mm. Style length: About 7.5 cm. Style color: Close to NN155D. Stigma length: About 1.5 mm to 2 mm. Stigma shape: Bipartite; narrowly linear; reflexed. Stigma color: Close to NN155D. Ovary color: Close to 144A.

*Seeds and fruits*.—To date, seed and fruit production has not been observed on plants of the new *Salvia*.

Pathogen & pest resistance: To date, plants of the new *Salvia* have not been noted to be resistant to pathogens and pests common to *Salvia* plants.

Garden performance: Plants of the new *Salvia* have exhibited good garden performance and to be tolerant to rain, wind and temperatures from about 5° C. to 40° C.

It is claimed:

1. A new and distinct *Salvia* plant named 'DPWSA-FUWHT' as herein illustrated and described.

* * * * *